(12) United States Patent
Lavallee et al.

(10) Patent No.: US 7,672,709 B2
(45) Date of Patent: Mar. 2, 2010

(54) DETERMINATION OF THE POSITION OF A RADIOGRAPHIC OR RADIOSCOPIC UNIT

(75) Inventors: Stéphane Lavallee, Saint Martin d'Uriage (FR); Guillaume Champleboux, Voiron (FR); Laurent Desbat, Grenoble (FR)

(73) Assignee: Perception Raisonnement Action en Medecine, La Tronche (FR)

( * ) Notice: Subject to any disclaimer, the term of this patent is extended or adjusted under 35 U.S.C. 154(b) by 1018 days.

(21) Appl. No.: 10/518,724

(22) PCT Filed: Jun. 20, 2003

(86) PCT No.: PCT/FR03/01917

§ 371 (c)(1),
(2), (4) Date: Jul. 8, 2005

(87) PCT Pub. No.: WO04/000122

PCT Pub. Date: Dec. 31, 2003

(65) Prior Publication Data

US 2006/0155189 A1    Jul. 13, 2006

(30) Foreign Application Priority Data

Jun. 20, 2002 (FR) .................................. 02 07726

(51) Int. Cl.
*A61B 5/05* (2006.01)
(52) U.S. Cl. ..................................................... 600/426
(58) Field of Classification Search ................ 600/443, 600/426, 410, 414, 407, 424, 439, 437; 606/99, 606/88, 10, 130; 382/128, 131; 324/318; 250/208.1; 378/21, 37, 61–63, 18
See application file for complete search history.

(56) References Cited

U.S. PATENT DOCUMENTS

| | | | |
|---|---|---|---|
| 5,836,954 A | 11/1998 | Heilbrun et al. | |
| 6,006,127 A | 12/1999 | Van Der Brug et al. | |
| 6,074,394 A | 6/2000 | Krause | |
| 6,285,902 B1 | 9/2001 | Kienzle, III et al. | |
| 6,990,368 B2 * | 1/2006 | Simon et al. ................. | 600/425 |
| 7,117,027 B2 * | 10/2006 | Zheng et al. ................. | 600/426 |
| 2004/0068187 A1 * | 4/2004 | Krause et al. ................ | 600/443 |

FOREIGN PATENT DOCUMENTS

| | | |
|---|---|---|
| WO | WO 00/48507 | 8/2000 |
| WO | WO 02/062249 A1 * | 8/2002 |

OTHER PUBLICATIONS

International Search Report dated Nov. 17, 2003 for related PCT Application No. PCT/FR03/01917.

* cited by examiner

*Primary Examiner*—Eric F Winakur
*Assistant Examiner*—Lawrence N Laryea
(74) *Attorney, Agent, or Firm*—Leason Ellis LLP

(57) ABSTRACT

The invention relates to a method for the determination of the position of a radiographic or radioscopic unit (16) with relation to a reference point ($R_{ref}$) on producing a radiographic image of an object (10). The position of the unit (16) with relation to a reference point ($R_{ref}$) is determined from the determination of the position of a test pattern (25), with relation to the unit (16), which is mechanically fixed to the object, by using the image of the test pattern with relation to the reference point ($R_{ref}$). The invention further relates to a determining device for carrying out said method.

15 Claims, 4 Drawing Sheets

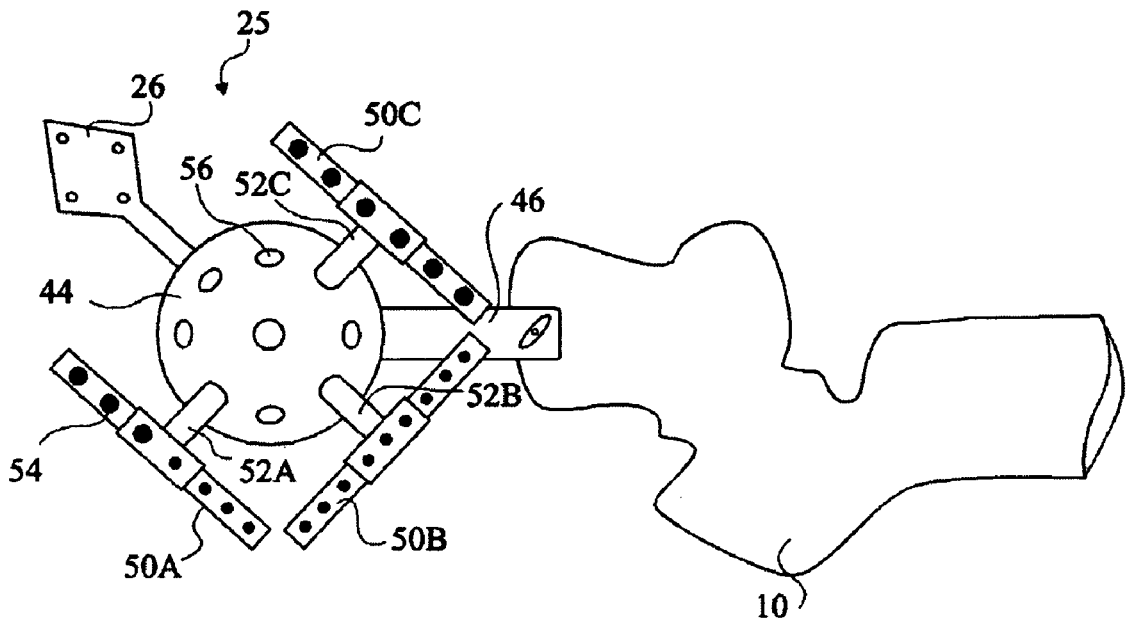
Fig 6
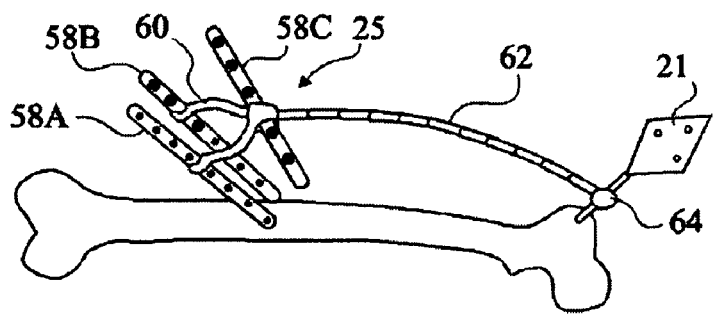
Fig 7
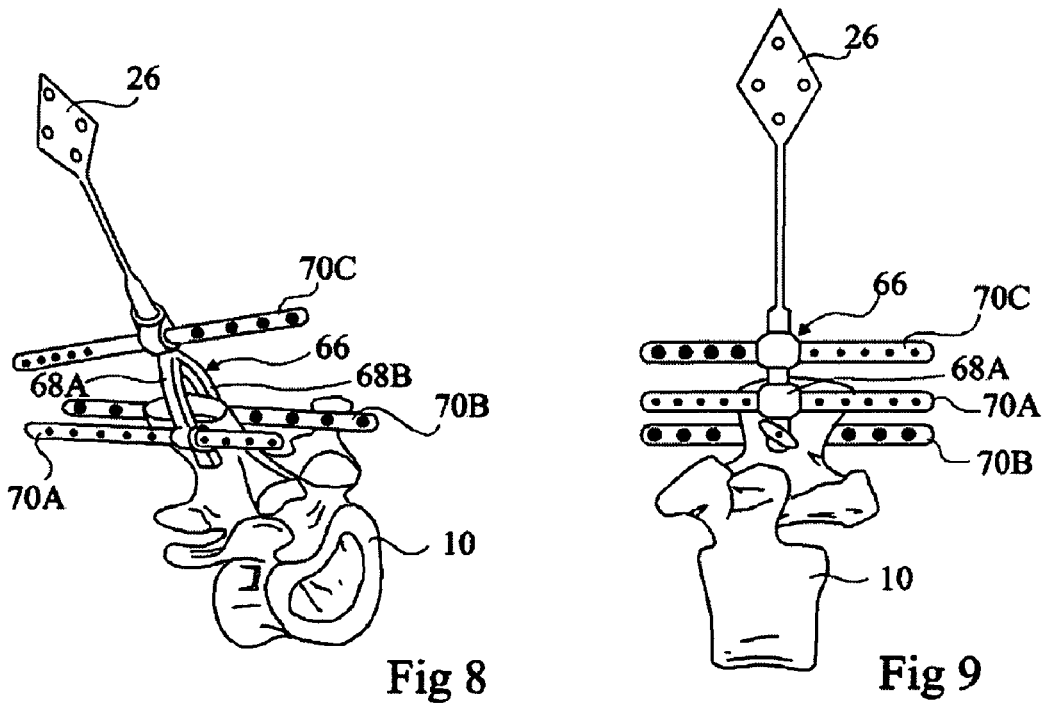
Fig 8
Fig 9

DETERMINATION OF THE POSITION OF A RADIOGRAPHIC OR RADIOSCOPIC UNIT

CLAIM FOR PRIORITY

This application is the national stage application under 35 U.S.C. §371 of the International Application No. PCT/FR2003/01917, and claims the benefit of French Application No. 02/01726, filed Jun. 20, 2002 and Int'l. Application No. PCT/FR03/01917, filed Jun. 20, 2003, the entire disclosures of which are incorporated herein by reference in their entireties.

The present invention relates to a method and a device for detecting the position in space of a device providing images by means of X rays, for example, a radiography or radioscopy device. Hereafter, any radiography or radioscopy device comprising an X-ray source, an X-ray photographic plate type sensor, and a film digitization system, or a radiography or radioscopy system formed of an X-ray source and of a digital sensor, or any operating suite device of mobile C-shaped arm type, comprised of a source and of an analog or digital sensor, the source and the sensor being rigidly interconnected, will be designated as a radiographic device.

For certain surgical operations, the surgeon may previously have three-dimensional images of the patient's region to be operated, obtained for example by means of a scanner. The images enable the surgeon to prepare the operation. During the operation, the surgeon may need to know the exact position of a bone with respect to the tools or of a pin that he is inserting. It is then no longer possible to perform a scanning to know such positions.

Radiographies under several angles of the patient's operated region are then usually acquired by means, for example, of a radiographic device. The radiographies are then digitized and the different elements present on the images are identified. By means of calculation algorithms, the elements identified on the radiographies can then be associated with the corresponding elements of the scanner views and the respective positions, for example, of a pin and of tools can be determined. The determination of the position of pins or tools with respect to the considered anatomic part or the anatomic region is performed by using a tracking system to which is associated a reference frame called $R_{ref}$. The tracking system may be based on an optical technology (such as system POLARIS of NDI Company, Toronto, Canada), based on a magnetic technology (such as system Fastrack of Polhemus Inc., USA), based on an ultrasound technology (product of Zebris Company, Germany). The tracking system locates in reference frame $R_{ref}$ the position of a rigid localization body by providing a transformation matrix between the reference frame associated with the rigid localization body and the reference frame associated with the tracking system. The rigid localization bodies may be formed of either emitter or receiver, or reflector, or re-emitter elements, according to the technology used.

When a rigid localization body is for example fixed to a vertebra and a rigid reference body is fixed to a surgical instrument, it is possible to control the position of the surgical instrument, the trajectory and/or the position of the instrument being determined due to the radiographic images provided a radiographic device. To be able to use the information contained in the radiographic images, it is necessary to determine the parameters of the radiographic device and to link the reference frame associated with the radiographic device and the reference frame of the localization system.

The obtaining of radiographies and their use require a previous step of determination of the operating parameters of the radiographic device, which is formed of a source projecting X-rays on an exposition surface, the object to be X-rayed being interposed between the source and the exposition surface. In more detailed fashion, the case in point is to model the projection performed by the radiographic device. A projection is the operation which, to a point (x, y, z) in the three-dimensional space, associates a point (u, v) in the image obtained on the exposition surface when an X-ray photograph is taken. The so-called back-projection lines D(u, v) are determined, each line corresponding to all the three-dimensional points in the space which project on pixel (u, v) of the image. The determination step enables obtaining the equations of the back-projection lines in reference frame $R_{amp}$ associated with the radiographic device. This amounts to determining so-called intrinsic parameters which are inherent to the geometry, to the manufacturing of the radiographic device, and to the method of digitization of the obtained image, and determining the so-called extrinsic parameters, which correspond to the transformation between the reference frame of radiography system $R_{amp}$ and fixed reference frame $R_{ref}$. If the radiographic device moves, there then remains to find the extrinsic parameters again. The algorithms for determining these parameters are described in document "The calibration problem for stereo by O. D. Faugeras et al." in Proc. Computer Vision and Pattern Recognition p. 15-20, 1992).

The determination step may be obtained by using a determination target (calibration target) attached to the radiographic device. The known methods and devices disclose:

a target-holding robot in "Gestes medico-chirurgicaux assistés par ordinateur", S. Lavallee Ph.D. Thesis, 1989, a target attached on the sensor described in document "Vissage pédiculaire assisté par ordinateur", P. Sautot, Ph.D. Thesis, 1994.

There also exist commercial systems (target directly attachable on the sensor, as for example, the product sold by Traxtal Technologies Company, USA).

Once the determination step has been completed, and assuming that the equations of the back-projection lines are not modified with respect to reference frame $R_{amp}$ in displacements of the radiographic device, radiographies of the tool are taken along different directions. If, however, the distortion problems due to the terrestrial magnetic field are not negligible, it is possible by a simple system to correct the equations of the back-projection lines (for example, by attaching a set of markers at the sensor periphery, which are visible on the image, the analysis of the position variation on the image enables determining and quantifying the distortion variation).

The radiographies, the transformation between reference frame $R_{amp}$ and reference frame $R_{ref}$ being known, are used for the surgical navigation. One may for example:

project the position of a tool on the radiographic images;

readjust the radiographic images with images provided by an X scanner; perform three-dimensional reconstructions by tomography or by the use of deformable models (French patent no 9911848 filed on Sep. 17, 1999 by Laboratoire TIMC, entitled "Reconstitution de surfaces en trois dimensions par utilisation de modèles statistiques"—the inventors of which are Markus Fleute, Stéphane Lavallée, and Laurent Desbat).

U.S. Pat. No. 5,769,861 filed by Brainlab Med Computersyst and entitled "Method and device for localizing an instrument" and U.S. Pat. No. 6,370,224 of Sofamor Danek Group entitled "System and methods for the reduction and elimination of image artifacts in the calibration of X Ray imagers" can be mentioned. Product fluoronav™ of Sofamor Danek Company, USA, can also be mentioned. FIG. 1A schematically shows an object 10, for example, a patient's bone, to be X-rayed. Object 10 is motionless with respect to a fixed reference frame $R_{ref}$. Object 10 is placed between a source 12, represented by a point, and an exposition surface 13, represented by a fixed plane with respect to source 12, of a radiographic device 16. The radiography corresponds to image 14 obtained on exposition surface 13. Radiographic device 16, that is, source 12 and exposition surface 13, is intended to be displaced with respect to object 10 to take the different X-ray photographs.

It is desired to determine the equations of the back-projection lines (two lines 17, 18 being shown in FIG. 1) in reference frame $R_{ref}$ at the time when each photograph is taken to perform a subsequent processing of the obtained radiographies. It is thus necessary to determine the geometric transformation enabling passing from reference frame $R_{amp}$ to reference frame $R_{ref}$ for each shooting.

A rigid localization body 19 is assembled on radiographic device 16 to be motionless with respect to reference frame $R_{amp}$. A localization system motionless in reference frame $R_{ref}$ is capable of determining the position of rigid body 19 in reference frame $R_{ref}$.

At the time when a radiography is performed, the position of mobile body 19 with respect to reference frame $R_{ref}$ is measured. It is then possible to determine the geometric transformation enabling passing from reference frame $R_{amp}$ to reference frame $R_{ref}$ at the time when the X-ray photograph is taken. It is thus possible to determine the equations of the back-projection lines with respect to reference frame $R_{ref}$ at the time when the photograph is taken.

Generally, two radiographies in different positions are acquired. For each radiography, the equations of the back-projection lines with respect to reference frame $R_{ref}$ are determined. By triangulation, it is then possible to determine a three-dimensional representation of object 10 that can be compared with preoperative images.

FIG. 1B shows elements of FIG. 1A. A rigid reference body 21, having its position determined by localization system 20, is attached on object 10 to be X-rayed and enables detecting the possible displacements of the object with respect to reference frame $R_{ref}$. A rigid body 22 may be placed on a surgical tool 23, having a mark on radiographic image 14 that can be represented. The position of tool 23 can thus be determined and used on analysis of the radiographic image. A target 24 (for example, an anatomic point, or the point of insertion of a screw . . . ) leaving a mark on the radiographic image can be aimed at on object 10 by tool 23.

The previously-described method for performing radiographies assumes a perfect synchronization between the obtaining of the radiography by radiographic device 16 and the measurement by localization system 20 of the position of rigid body 19 solid with radiographic device 16.

To ensure the synchronization, a system which detects the emission of X rays by radiography tool 16 may be used at the time when a radiography is performed, and then automatically controls the memorization by localization system 20 of the position of radiography tool 16 at the time when the photograph is taken. The acquisition of the radiography and the memorization of the position of radiography tool 16 may also be controlled by a processor simultaneously connected to radiographic device 16 and to localization system 20.

However, such systems are difficult to form and require using expensive sensors or devices.

The present invention aims at providing a method and a device for detecting the position of a radiographic device where an X-ray photograph is taken which does not exhibit the abovementioned disadvantages.

To achieve this object, the present invention provides a method for determining the position of a device providing images by means of X rays with respect to a reference frame as an image of an object is taken, in which the position of the device with respect to the reference frame is determined based on the determination of the position with respect to the device of a target, mechanically connected to the object, by means of the impression of the target on the image, and on the determination of the position of the target with respect to the reference frame.

According to an embodiment of the present invention, the position of the target with respect to the reference frame is determined from the determination, by a localization system, of the position with respect to the reference frame of a rigid localization body mechanically connected to the target.

According to an embodiment of the present invention, the target is fixed with respect to the rigid body.

According to an embodiment of the present invention, the configuration of the target is determined by a feeler connected to a rigid localization body having its position with respect to the reference frame determined by a localization system.

According to an embodiment of the present invention, the target is connected to the rigid body by an articulated arm.

According to an embodiment of the present invention, the target is removed from the object between the acquisition of two images.

According to an embodiment of the present invention, the determination of the position of the target with respect to the device is performed from the determination on the image of characteristic impressions, each characteristic impression corresponding to the projection on the image of a separate element of the target.

The present invention also provides a target comprising elements transparent to X rays and elements opaque to X rays, comprising at least three supports transparent to X rays, each support containing balls opaque to X rays substantially aligned along a determined direction, the determined directions being non coplanar.

According to an embodiment of the present invention, at least two balls are of different diameters.

According to an embodiment of the present invention, the target comprises a holding means capable of maintaining the cylinders according to a configuration from among several determined configurations.

The present invention also provides a device for determining the position of a device providing images by means of X rays with respect to a reference frame when a radiography of an object is acquired, comprising a target connected to the object and comprising elements opaque to X rays, each opaque element being capable of providing a characteristic impression on the radiography of the object; a means for determining the position of the target with respect to the reference frame; and a means for determining the position of the target with respect to the radiographic device based on the characteristic impressions of the radiography.

The foregoing object, features, and advantages, as well as others of the present invention will be discussed in detail in the following non-limiting description of specific embodiments in connection with the accompanying drawings, among which:

FIG. 1A, previously described, illustrates in simplified fashion a conventional method for performing radiographies;

FIG. 1B, previously described, illustrates the use of radiographic images to localize the position of a tool with respect to a determined target;

FIG. 2 schematically illustrates a method for performing radiographies according to the present invention;

Figure 3:
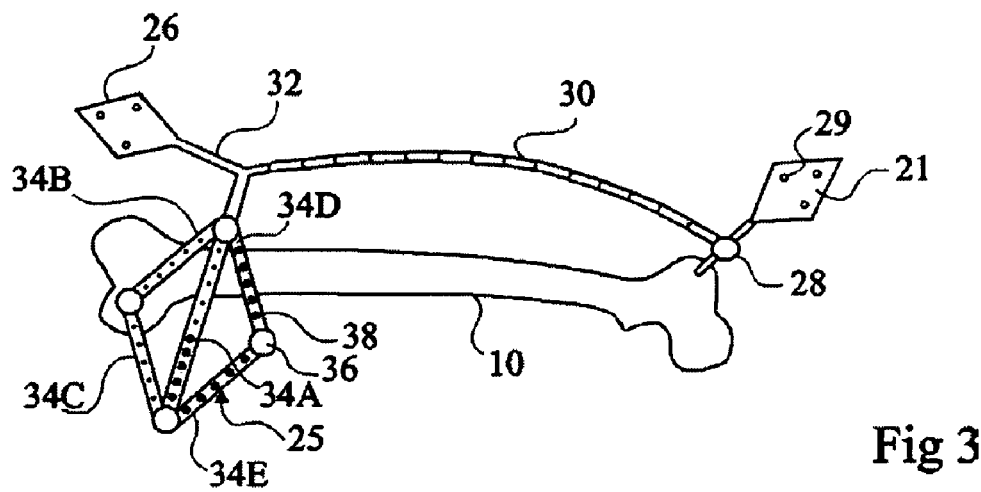
FIG. 3 shows an example of the forming of a target according to the present invention.
Figure 5:
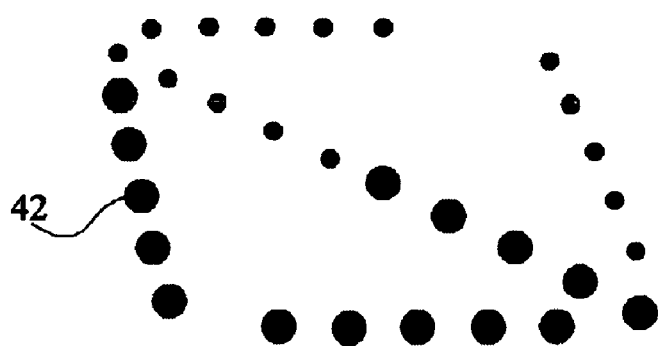
Figure 10:
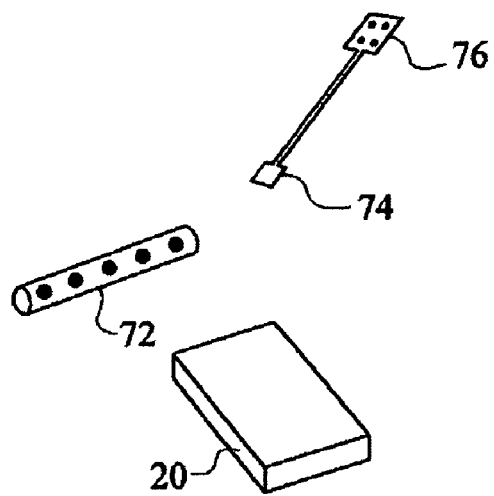
Figure 11:
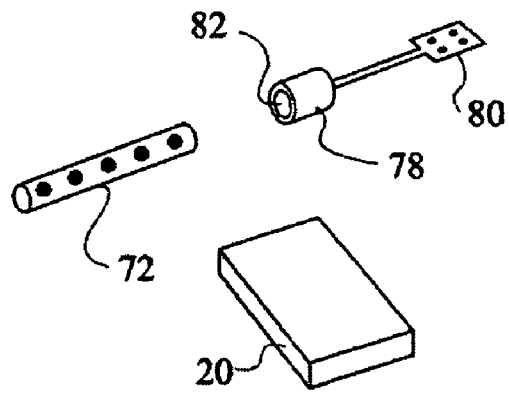
Figure 12:
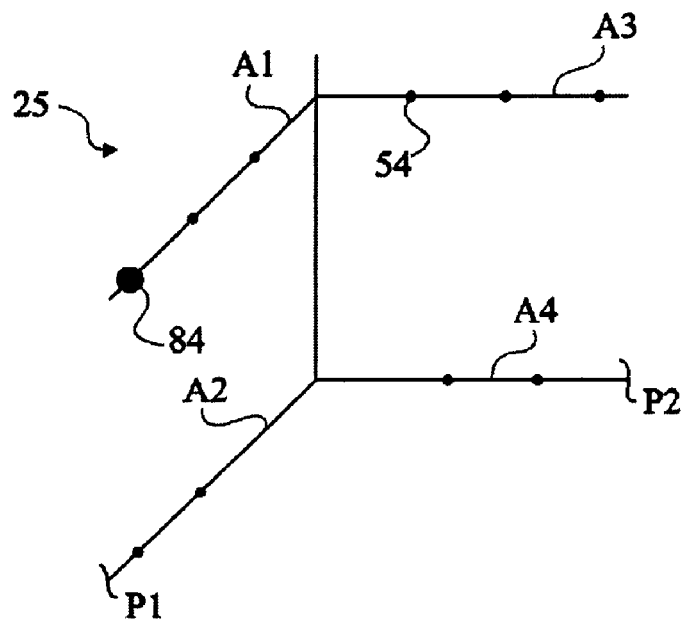
Figure 13:
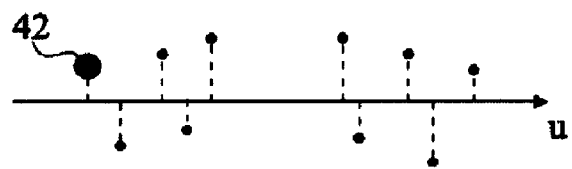

FIG. 5 schematically shows an example of a radiography of the target of FIG. 3;

FIGS. 6 and 7 shows two variations of the target of FIG. 3;

FIGS. 8 and 9 show two views of another variation of the target according to the present invention;

FIGS. 10 and 11 show examples of determination of the target configuration;

FIG. 12 schematically shows another variation of the target according to the present invention; and FIG. 13 shows an example of a radiography of the target of FIG. 12.

The present invention provides a device, the use of which enables determining the geometric transformation enabling passing from reference frame $R_{amp}$ to initial reference frame $R_{ref}$ at the time when a radiography is taken by directly using the image of an element of the device obtained on the radiography. The intrinsic parameters of the radiographic device may be previously determined according to a conventional procedure such as described in the document entitled "Vissage pédiculaire assisté par ordinateur" by P. Sautot, Ph. D. Thesis, 1994. The present invention provides a device, the use of which simplifies existing methods for determining the extrinsic parameters when the radiographic device has been displaced.

Figure 1A:
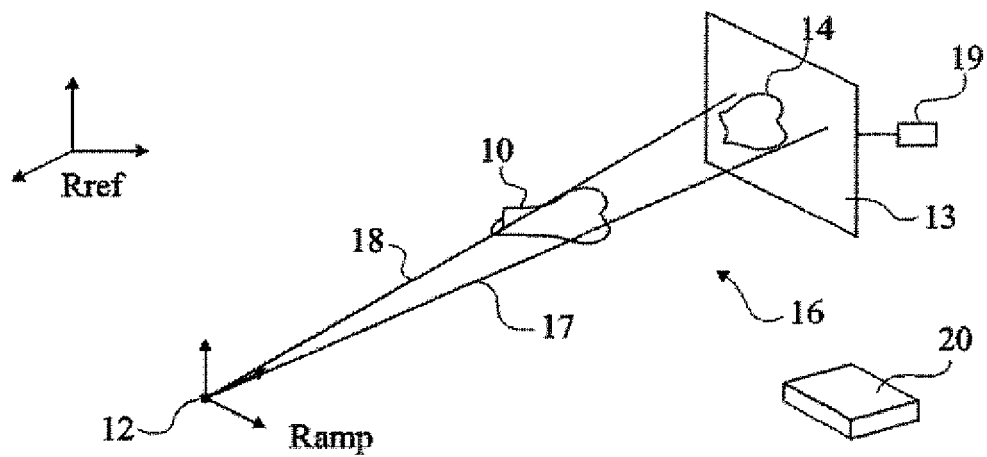
Figure 1B:
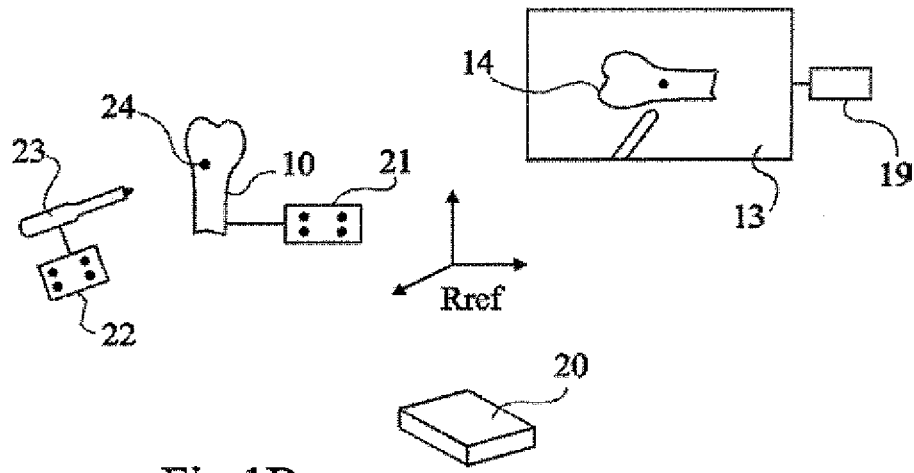
Figure 2:
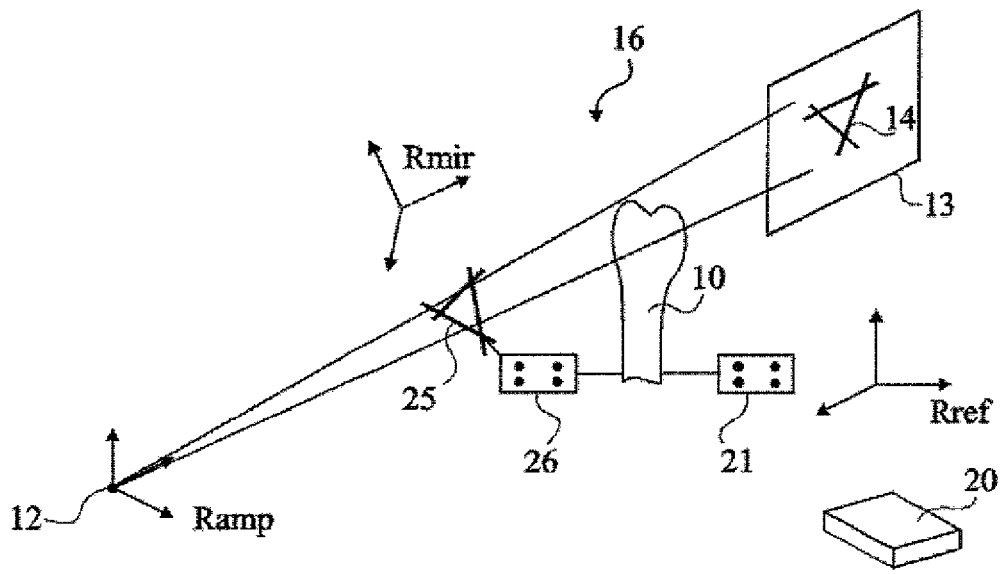

FIG. 2 shows source 12 of the radiographic device capable of emitting X rays crossing object 10 to be X-rayed to form an image 14 on exposition surface 13. A target 25 and a rigid body 26 are assembled on object 10 to be X-rayed. Rigid body 26 is fixed with respect to a reference frame $R_{mir}$ associated with target 25.

The method for acquiring radiographies of object 10 according to the present invention is the following. Prior to the radiographies, the equations of the back-projection lines, expressed in reference frame $R_{amp}$, are determined. The position of rigid body 26 with respect to initial reference frame $R_{ref}$ is also determined. The relative positions between rigid body 26 and target 25 being known, it is possible to determine the geometric transformation T1 enabling passing from reference frame $R_{mir}$ associated with target 25 to initial reference frame $R_{ref}$. After, between several shootings, target 25 and object 10 are superposed fixedly with respect to initial reference frame $R_{ref}$, and geometric transformation T1 remains constant. If such was not the case, T1 should be determined again.

Radiographic device 16 is then displaced to different positions to perform radiographies. For each radiography, the analysis of the obtained image 14 enables, due to the presence of target 25 on object 10 and as will be explained hereafter, determining the geometric transformation T2 enabling passing from reference frame $R_{amp}$ associated with radiographic device 16 to reference frame $R_{mir}$ associated with target 25.

It is thus possible to determine the general geometric transformation TG enabling passing from reference frame $R_{amp}$ associated with the radiographic device 16 to initial reference frame $R_{ref}$. The equations of the back-projection lines in initial reference frame $R_{ref}$ can then be determined, and may be used to define a three-dimensional image of object 10 as explained previously.

FIG. 3 more specifically shows an example of a form of target 25. A base 28 is temporarily attached to object 10 to be X-rayed, for example, a patient's femur. Base 28 supports rigid reference body 21 which comprises, for example, elements 29 capable of reflecting the infrared rays emitted by localization system 20. A flexible shaft 30 connects base 28 to a fork 32 which supports mobile body 26 at the end of a branch and target 25 at the end of the other branch.

It should be noted that target 25 and attached rigid body 26 could also be, for example, simply placed on the object 10, or placed on the operating table, or clipped to a surgical drape, etc. . . . , provided that target 25 is in the field of view of the X-ray image and rigid body 26 is in the field of view of the tracking system 20 at the instant the X-ray image is acquired.

Target 25 is formed of several cylinders, 34A to 34E, connected at their ends by junction spheres 36. Each cylinder 34A to 34E is formed of a material transparent to X rays, for example a plastic matter or a material known under trade name Plexiglas, and comprises balls opaque to X rays 38, for example made of tungsten carbide, of lead, or of steel, substantially aligned along the axis of cylinder 34A to 34E.

Target 25 is formed of a central cylinder 34A, comprising for example five balls 38 of a first diameter, for example, six millimeters and, for example, five balls 38 of a second diameter, for example, three millimeters, smaller than the first diameter, the balls of the first diameter being located on one half of central cylinder 34A and the balls of the second diameter being located on the second half. Two secondary cylinders 34B, 34C, comprising balls 38 of the second diameter, form with central cylinder 34A a first triangle. Two secondary cylinders 34D, 34E, comprising balls 38 of the first diameter, form with central segment 40 a second triangle. The planes containing the two triangles are inclined with respect to each other.

Figure 4:
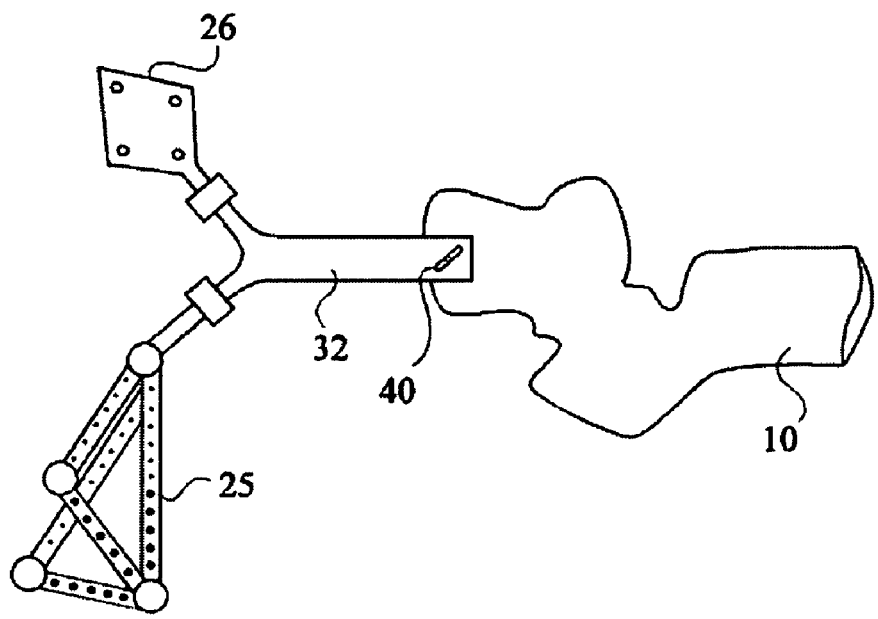
FIG. 4 shows a variation of the target of FIG. 3.

FIG. 4 shows an alternative of the device of FIG. 3. Fork 32 is directly assembled on object 10 to be X-rayed by an attachment means 40. According to this alternative, target 25 being fixed with respect to object 10, a single rigid body 26 may be used directly to define the position of target 25 and of object 10 with respect to initial reference frame $R_{ref}$ and the geometric transformation T2 enabling passing from reference frame $R_{mir}$ to initial reference frame $R_{ref}$.

FIG. 5 shows an example of a radiography obtained from mobile target 25 of FIG. 3 assembled on object 10 to be X-rayed. Balls 38 opaque to X rays leave circular marks 42 on the radiography. Cylinders 34A to 34B transparent to X rays leave substantially no mark on the radiography. Object 10 also leaves marks on the radiography which can superpose to those of balls 38 and which are not shown in FIG. 5. The obtained radiography is digitized. By using an appropriate algorithm, circular marks 42 are determined. The positions of the centers of circular marks 42, as well as segments of straight lines crossing said centers, are then calculated. It is then determined to which cylinder 34A to 34E of mobile target 25 does each segment of a straight line correspond, by especially using the diameter difference of balls 42 and their distribution per cylinder 34A to 34E.

The equations of the back-projection lines of each pixel of the radiography are known in reference frame $R_{amp}$ associated with radiographic device 16. Based on the back-projection lines, the shape of target 25 being perfectly well known, it is possible to determine the position that target 25 must have in reference frame $R_{amp}$ to generate marks 42 obtained on the radiography. This may be obtained by the minimization of a quadratic criterion. The geometric transformation T2 enabling passing from reference frame $R_{amp}$ 25 associated with the radiographic device to reference frame $R_{mir}$ associated with target 25 is thus determined.

FIG. 6 shows an alternative forming of target 25 according to the present invention. Target 28 is formed of a junction sphere 44 assembled on a holding arm 46 attached on object 10 to be X-rayed. Cylinders 50A, 50B, 50C are assembled on junction sphere 44 by attachment branches 52A, 52B, 52C.

Rigid body 26 is also assembled on junction sphere 44. Cylinders 50A, 50B, 50C are, as previously explained, formed of a material transparent to X rays and comprise balls 54 opaque to X rays. The different cylinders 50A, 50B, 50C must preferably be arranged not to be coplanar. Junction sphere 44 comprises additional openings 56 distributed across its entire surface possibly enabling adding additional cylinders or arranging the three cylinders according to a different configuration.

FIG. 7 shows another alternative of target 25 according to the present invention. Two cylinders 58A, 58B are attached to the ends of the arms of a fork 60. A third cylinder 58C is attached to the base of fork 60. Target 25 is connected by a flexible rod 62 to a mount 64 attached to object 10 to be X-rayed. Rigid reference body 21 is attached solid with mount 64. According to this alternative, there is no mobile body attached solid with target 25. In the determination of geometric transformation T1 enabling passing from reference frame $R_{mir}$ to initial reference frame $R_{ref}$, the determination of the position of target 25 with respect to rigid reference body 21 may be obtained by means of a feeler.

FIGS. 8 and 9 show two views of another variation of target 25. Object 10 to be X-rayed is for example a vertebra. Target 25 comprises a fork 66 having its arms 68A, 68B attached to object 10. Each arm 68A, 68B supports a cylinder 70A, 70B. A third cylinder 70C is attached to the base of fork 66. Rigid body 26 is also attached to the base of fork 66. According to this alternative, target 25 being fixed with respect to object 10, a single rigid body 26 may be used directly to define the positions of target 25 and of object 10 with respect to initial reference frame $R_{ref}$ and to determine the geometric transformation T1 enabling passing from reference frame $R_{mir}$ to reference frame $R_{ref}$.

FIGS. 10 and 11 show examples of the determination of the target configuration (a single cylinder 72 of the target being shown in FIGS. 10 and 11) in the case where said mark is assembled on the object in a non-predefined manner, as can be the case with the examples of the forming of the target shown in FIGS. 3, 6, and 7. A feeler 74 connected to a rigid body 76, having its position determined by localization system 20, may be displaced on the target to determine its shape. A specific feeler of recessed-type 78 with a single position connected to a rigid localization body 80 and comprising a hollow cylinder 82 of a diameter corresponding to the diameter of target cylinders may also be used. Recessed system 78 is then adjusted on each of the target cylinders.

FIG. 12 schematically shows another alternative of target 25 according to the present invention. According to such an alternative, target 25 comprises ten opaque balls 54, nine balls having an identical diameter and one ball 84 having a greater diameter. Balls 54 are distributed in two planes P1 and P2, five balls being associated with each plane. The angle between planes P1 and P2 is strictly smaller than 180 degrees and, advantageously, on the order of 90 degrees. In plane P1, the balls are distributed along two parallel axes A1, A2. Three balls are arranged substantially equidistantly on axis A1 and two balls are arranged along axis A2 in quincunx with respect to the balls of axis A1. The largest ball 84 is placed at the end of axis A1 most distant from plane P2. In plane P2, the balls are distributed along two parallel axes A3, A4. Three balls are distributed equidistantly on axis A3 and two balls are arranged on axis A4 in quincunx with respect to the balls of axis A3. Axis A1 cuts axis A3 and axis A2 cuts axis A4. The plane defined by axes A1 and A3 forms with plane P1 an angle of approximately 90 degrees.

Target 25 must remain visible on exposition surface 13 whatever the displacement of source 12 and of exposition surface 13. In the case where source 12 and exposition surface 13 move on a sphere having its center corresponding to object 10, the source and the exposition surface being diametrical, target 25 must be comprised within a sphere, centered on object 10, having its radius r provided by the following relation:

$$r = d*\sin(\alpha)/2 \text{ with } \tan(\alpha) = l/2d$$

where d is the distance between source 12 and exposition surface 13 and l is the width of exposition surface 13.

Axis A1 (respectively, A3) and axis A2 (respectively A4) are as spaced apart as possible, while respecting the previously-stated condition concerning the dimensions of target 25, to improve the numerical stability of the algorithm which determines the positions of the circular marks corresponding to the images of balls 54 on exposition surface 13.

FIG. 13 shows an example of a radiography obtained from mobile target 25 of FIG. 12. The applicant has shown that with the structure of target 25, the order of circular marks 42 along a direction u is identical almost independently from the positions of source 12 and of exposition surface 13 with respect to target 25. The dimensions of target 25 being sufficiently small with respect to distance d, circular mark 42 associated with the largest ball 84 is greater than the circular marks associated with the other balls. Thereby, by placing the largest ball 84 so that the associated circular mark 42 is at the first position along direction u, the putting in correspondence of circular marks 42 and balls 54 is then trivial. Direction u for example corresponds to a direction characteristic of exposition surface 13 or to the main axis of inertia of circular marks 42.

The use of ten balls contributes to the robustness of the circular mark detection algorithm. However, target 25 may comprise less than ten balls without excessively degrading the robustness of the detection algorithm. Two balls on axis A1 (including the largest ball), one ball on axis A2, two balls on axis A3, and one ball on axis A4, may for example be provided.

The present invention has many advantages.

First, the present radiography method enables determining the geometric transformation between reference frame $R_{amp}$ associated with the radiographic device and initial reference frame $R_{ref}$ when a radiography is performed, directly from the radiography by the analysis of the impression left on the radiography by a target attached to the object to be X-rayed. It is then not necessary to permanently attach a rigid body to the radiographic device, since the analysis of the impression of the target on the radiography enables following the motion of the radiographic device and finding the rigid spatial transformations between two different positions.

Second, the target may be formed in a light material to be able to be attached on the object to be X-rayed. In particular, the target does not hinder possible displacements of the object, in the case where for example the object is a vertebra. For example, the target may weight less than 300 grams.

Third, the shape of the target may easily be adapted according to the object to be X-rayed and/or to the surgical operation to be performed to avoid hindering the surgeon's gestures.

Of course, the present invention is likely to have various alterations and modifications which will occur to those skilled in the art. In particular, the opaque balls may be distributed on element other than cylindrical. They may for example be transparent tubes describing three-dimensional curves. Further, there may be more than two different diameters for the opaque balls. Finally, some of the features of the previously-described examples of embodiment may be combined.

The invention claimed is:

1. A method for determining the position of a device providing images by X rays with respect to a reference frame as an image of an object is taken, said method comprising the steps of:
    determining the position of a target with respect to the device, said target mechanically connected to the object, based on an impression of the target on the image of the object;
    determining the position of the target with respect to the reference frame; and
    determining the position of the device with respect to the reference frame based on the position of the target with respect to the device, and the position of the target with respect to the reference frame.

2. The method of claim 1, in which the position of the target with respect to the reference frame is determined from the determination, by a localization system, of the position with respect to the reference frame of a rigid localization body mechanically connected to the target.

3. The method of claim 2, in which the target is fixed with respect to the rigid body.

4. The method of claim 1, in which a configuration of the target is determined by a feeler connected to a rigid localization body, the position of the feeler with respect to the reference frame being determined by a localization system.

5. The method of claim 2, in which the target is connected to the rigid body by an articulated arm.

6. The method of claim 1, in which the target is removed from the object between an acquisition of a first image and an acquisition of a second image.

7. The method of claim 1, in which the determination of the position of the target with respect to the device is performed from the determination on the image of the impression of the target, said impression comprising a plurality of characteristic impressions, each of said plurality of characteristic impressions corresponding to a projection on the image of a separate element of the target.

8. The method of any of claims 1 to 7, wherein the target comprising:
    a plurality of elements transparent to X rays;
    a second plurality of elements opaque to X rays; and
    wherein said first plurality of elements comprises at least three supports transparent to X rays, each support containing said second plurality of elements comprising a plurality of balls opaque to X rays substantially aligned along a determined direction, the determined directions being non coplanar.

9. The method of claim 8, in which at least two balls of said plurality of balls are of different diameters.

10. The method of claim 8, wherein said target further comprises a hold means capable of maintaining the at least three supports according to a configuration from among several determined configurations.

11. A system for determining the position of a device providing image by X rays with respect to a reference frame when a radiography of an object is acquired, said system comprising:
    a target connected to the object and comprising a plurality of elements opaque to X rays, each of said plurality of opaque elements being capable of providing a characteristic impression on the radiography of the object;
    a means for determining the position of the target with respect to the reference frame;
    a means for determining the position of the target with respect to the device based on the characteristic impressions of the radiography,
    wherein said system is adapted to determine the position of the device with respect to a reference frame based on the position of the target with respect to the reference frame on the position of the target with respect to the device.

12. A method for determining the position of a device providing images by X rays with respect to a reference frame as an image of an object is taken, said method comprising the steps of:
    determining the position of a target with respect to said device based on an impression of said target on the image of said object, said target being mechanically connected to the object and including a plurality of elements opaque to X rays which define the impression of the target;
    determining the position of said target with respect to the reference frame using a rigid body that is mechanically connected to said target; and
    determining the position of the device with respect to the reference frame based on the position of said target with respect to said device, and the position of said target with respect to the reference frame.

13. The method of claim 12, wherein the target includes a plurality of elements transparent to X rays that includes at least three supports transparent to X rays, each support containing the opaque elements comprising a plurality of balls opaque to X rays, the balls being substantially aligned along a determined direction, the determined directions being non coplanar.

14. The method of claim 13, in which at least two balls of said plurality of balls are of different diameters.

15. The method of claim 13, wherein said target further comprises a hold means capable of maintaining the at least three supports according to a configuration from among several determined configurations.

* * * * *